United States Patent [19]

Steigelmann et al.

[11] Patent Number: 5,118,896
[45] Date of Patent: Jun. 2, 1992

[54] AROMATIC ALKYLATION PROCESS USING LARGE MACROPORE, SMALL PARTICLE SIZE, ZEOLITE CATALYST

[75] Inventors: Edward F. Steigelmann, Naperville; Terry L. Marker, Warrenville, both of Ill.

[73] Assignee: Amoco Corporation, Chicago, Ill.

[21] Appl. No.: 606,100

[22] Filed: Oct. 31, 1990

[51] Int. Cl.$^5$ .............................................. C07C 2/66
[52] U.S. Cl. ....................................... 585/467; 585/453
[58] Field of Search .................. 585/467, 446, 453; 203/DIG. 6

[56] References Cited

U.S. PATENT DOCUMENTS

| | | | |
|---|---|---|---|
| 3,308,069 | 3/1967 | Wadlinger et al. | 208/120 |
| 3,929,672 | 12/1975 | Ward | 502/66 |
| 4,016,218 | 4/1977 | Haag et al. | 585/467 |
| 4,157,950 | 6/1979 | Frilette et al. | 585/467 X |
| 4,301,316 | 11/1981 | Young | 585/467 X |
| 4,459,267 | 7/1984 | Inwood et al. | 585/467 X |
| 4,570,027 | 2/1986 | Boucher et al. | 585/467 X |
| 4,665,255 | 5/1987 | Chang et al. | 585/467 |
| 4,795,847 | 1/1989 | Weitkamp et al. | 585/467 |
| 4,837,396 | 6/1989 | Herbst et al. | 502/67 |
| 4,891,458 | 1/1990 | Innes et al. | 585/467 X |
| 4,899,008 | 2/1990 | LaPierre et al. | 585/467 |

OTHER PUBLICATIONS

Kirk-Othmer, *Encyclopedia of Chemical Technology*, 3rd Ed., vol. 5, pp. 19 and 20 (1970).

*Primary Examiner*—W. J. Shine
*Assistant Examiner*—Douglas J. McGinty
*Attorney, Agent, or Firm*—Reginald K. Taylor; William H. Magidson; Frank J. Sroka

[57] ABSTRACT

An aromatic alkylation process comprising the steps of contacting a hydrocarbon feed comprising an aromatic hydrocarbon with an alkylating agent under liquid phase alkylation condition in the presence of a silica-containing molecular sieve wherein said said catalyst possesses a pore volume of about 0.25–0.50 cc/g in pores having a radius greater than 450 Angstroms and a catalyst particle diameter of not more than about 1/32 of an inch.

16 Claims, 3 Drawing Sheets

AROMATIC ALKYLATION PROCESS USING LARGE MACROPORE, SMALL PARTICLE SIZE, ZEOLITE CATALYST

FIELD OF THE INVENTION

The invention relates to an aromatic alkylation catalyst and process comprising the steps of contacting an aromatic hydrocarbon with an alkylating agent under liquid phase alkylation conditions in the presence of a catalyst comprising a silica-containing molecular sieve in a matrix comprising a porous refractory inorganic oxide wherein said catalyst possesses a pore volume of about 0.25–0.50 cc/g in pores having a radius greater than about 450 Angstroms and a catalyst particle diameter of not more than about 1/32 of an inch.

BACKGROUND OF THE INVENTION

Hydrocarbon conversion processes, particularly alkylation of aromatic hydrocarbons, are the foundation for the production of an assorted variety of useful petrochemicals. For instance, ethylbenzene and ethyltoluene, as well as other alkyl-substituted aromatics, are beneficial as feedstocks for the production of a variety of styrenic polymer materials, cumene, and detergent alkylates. Alkyl-substituted aromatics are also useful as high octane transportation fuels. The use of alkyl-substituted aromatics as blending agents for gasoline expands product volume and increases octane values. Aromatic alkylation processes also provide an economic method of reducing benzene content in gasoline.

In the past, alkylation processes have employed acidic catalysts such as $AlCl_3$, $FeCl_3$, $SbCl_5BF_3$, $ZnCl_2$, $TiCl_4$, HF, $H_2SO_4$, $H_3PO_4$, $P_2O_5$ and the like. Reactions using these catalysts are generally carried out at low temperatures and, in particular, when a Friedel-Craft catalyst is employed, in the presence of a hydrogen halide, such as HCl.

There are numerous problems associated with the use of these acidic catalysts in an alkylation process. First, these catalysts are very corrosive, thereby requiring the use of exotic materials for process equipment. Second, the catalyst consumption and the regeneration costs are high. Third, the yields of alkylate boiling in the gasoline range are low. Fourth, complicated separations and recycle of feed can be required. Fifth, these catalysts tend to polymerize the olefinic reagents, thus minimizing available starting materials.

Many of these problems have been avoided by using synthetic or natural zeolite materials as alkylation catalysts. Certain zeolitic materials are porous crystalline aluminosilicates having a definite crystalline structure within which there are a large number of smaller cavities which can be interconnected by a number of even smaller channels. Since the dimensions of these pores are such that molecules of a certain dimension are accepted for adsorption while larger molecules are rejected, these materials have come to be known as "molecular sieves".

A particular type of molecular sieve useful in aromatic alkylation reactions is a crystalline aluminosilicate zeolite. Crystalline aluminosilicate zeolites are composed of a rigid three-dimensional framework of $SiO_4$ and $AlO_4$ in which the tetrahedra are cross-linked by the sharing of oxygen atoms. The electrovalence of the tetrahedra containing aluminum is balanced by the inclusion in the crystal of a cation, such as an alkali metal or an alkaline earth metal. Since these cations are exchangeable, it is possible to vary the properties of a particular aluminosilicate by selection of a suitable cation.

The use of crystalline aluminosilicates in aromatic alkylation processes is well-known in the art. In U.S. Pat. No. 2,904,607 there is disclosed a process for alkylating aromatics with olefins in the presence of a crystalline metallic aluminosilicate having a uniform pore opening of about 6–15 Angstroms. In U.S. Pat. No. 3,251,897 there is disclosed a process for alkylating aromatics with a crystalline aluminosilicate which contains rare earth metal cations and a uniform pore volume of at least 6 Angstroms.

While the use of crystalline aluminosilicate zeolite catalysts in aromatic alkylation processes represent a distinct improvement over Friedel-Craft catalysts, zeolite catalysts have the disadvantage of producing unwanted quantities of impurities. They also deactivate at a rapid rate, particularly in vapor phase reaction zones. Consequently, the industry began treating zeolites to specifically address these deactivation and selectivity problems. In U.S. Pat. No. 2,897,246, there is disclosed heating a crystalline aluminosilicate in the presence of water vapor at a temperature of 400–900 deg C. prior to using it in an alkylation process. In U.S. Pat. No. 3,631,120, there is disclosed ammonium-exchanging a crystalline aluminosilicate to achieve a silica-to-alumina molar ratio of 4.0–4.9 prior to using it in an aromatic alkylation process. Other methods of treating a crystalline aluminosilicate for use in an aromatic alkylation process include steaming and ammonium-exchanging the zeolite (U.S. Pat. No. 3,641,177), rare earth-exchanging the zeolite in the presence of sulfur dioxide (U.S. Pat. No. 4,395,372), partially collapsing the zeolite to reduce crystallinity (U.S. Pat. No. 4,570,027), (U.S. Pat. No. 4,575,573), increasing the total amount of lattice metal in the zeolite (U.S. Pat. No. 4,665,255), reacting the zeolite with an acidic inorganic oxide in the presence of water (U.S. Pat. No. 4,665,253), and depositing carbonaceous material on the zeolite (U.S. Pat. No. 4,798,816).

New crystalline aluminosicates were also developed to address these selectivity and deactivation problems. U.S. Pat. Nos. 4,393,263, 4,291,185, 4,387,259, 4,393,262, and 4,469,908 disclose the use of ZSM-12 in an aromatic alkylation process. U.S. Pat. No. 4,547,605 discloses the use of ZSM-23 in an aromatic alkylation process. U.S. Pat. No.4,717,780 discloses the use of ZSM-58 in an aromatic alkylation process.

U.S. Pat. No. 4,185,040 discloses that the selectivity and deactivation problems associated with the use of crystalline aluminosilicates can be addressed by shaping the extrudates to give a high ratio of external surface area to crystal pore volume. Crystal pore diameter is defined as 5–15 Angstroms.

The process conditions used during aromatic alkylation can affect the performance of a crystalline aluminosilicate zeolite catalyst. For example, vapor phase aromatic alkylation processes, such as those disclosed in U.S. Pat. Nos. 3,751,504 and 3,751,506, generally have high conversions due to greater ease in the diffusion of the vapor reactants into the micropores of the crystalline aluminosilicate, but high catalyst deactivation rates due to olefins attaching to the active sites of the zeolite catalyst and coking up deactivating the catalyst. On the other hand, liquid phase aromatic alkylation processes, such as those described in U.S. Pat. Nos. 3,251,897 and 3,631,120, generally have lower conversion rates due to diffusional limitations, but low catalytic deactivation rates due the aromatics preferentially occupying the active sites of the zeolite catalyst, thereby preventing the olefins from deactivating the catalyst.

There is a need for an improved alkylation catalyst for use in a liquid phase aromatic alkylation process where the diffusion of liquid reactants into the catalyst has been a problem.

SUMMARY OF THE INVENTION

In its broadest aspect, the present invention is an aromatic alkylation process comprising the steps of contacting an aromatic hydrocarbon with an alkylating agent under liquid phase alkylation conditions in the presence of a catalyst comprising a silica-containing molecular sieve in a matrix comprising a porous refractory inorganic oxide wherein said catalyst possesses a pore volume of about 0.25–0.50 cc/g in pores having a radius greater than about 450 Angstroms and a catalyst particle diameter of not more than about 1/32 of an inch. Applicants have discovered that the combination of a high macropore volume and a small catalyst particle size results in a catalyst having improved diffusional access to its interior. The improved diffusional characteristic of such a catalyst is particularly useful in a liquid phase reaction where diffusion of the liquid reactants into the catalyst has been a problem. The presence of a liquid phase during aromatic alkylation can reduce the catalyst deactivation rate.

In one embodiment, the present invention is an aromatic alkylation process comprising the steps of contacting a liquid aromatic hydrocarbon selected from the group consisting of benzene, toluene, and xylene with an alkylating agent comprising an olefinic hydrocarbon under liquid continuous phase alkylation conditions in the presence of a catalyst comprising a crystalline aluminosilicate zeolite in a matrix selected from the group consisting of silica and alumina wherein said catalyst possesses a pore volume of about 0.25–0.35 cc/g in pores having a radius greater than about 450 Angstroms and a catalyst particle diameter of not more than about 1/64 of an inch, said catalyst being disposed in a fixed-bed, reactive-distillation reactor. By disposing the catalyst in a fixed-bed, reactive-distillation reactor, monoalkyl aromatics such as ethylbezene and propylbenzene are immediately removed from the reaction zone by fractionation, thereby reducing the amount of undesirable polyalkyl aromatics produced.

In another embodiment, the invention is an aromatic alkylation process comprising the steps of contacting a liquid aromatic hydrocarbon selected from the group consisting of benzene, toluene, and xylene with an gaseous alkylating agent comprising ethylene and propylene under liquid continuous phase alkylation conditions in the presence of a catalyst comprising beta zeolite in a matrix consisting essentially of alumina wherein said catalyst possesses a pore volume of about 0.25–0.35 cc/g in pores having a radius of greater than about 450 Angstroms and a catalyst particle diameter of not more than about 1/100 of an inch, said catalyst being employed in a plurality of solid porous containers disposed in a fixed-bed, reactive-distillation reactor.

In another embodiment, the present invention is an aromatic alkylation catalyst comprising a silica-containing molecular sieve in a matrix comprising a porous refractory inorganic oxide wherein said catalyst possesses a pore volume of about 0.25–0.50 cc/g in pores having a radius greater than about 450 Angstroms and a catalyst particle diameter of not more than about 1/32 of an inch. The benefits of this catalyst are higher activity and lower deactivation rate.

BRIEF DESCRIPTION OF THE DRAWINGS

FIG. 1 illustrates that, at a constant particle diameter (see Catalysts B and C), the higher the macropore volume, the higher the ethylene conversion and the lower the catalyst deactivation rate.

FIG. 2 illustrates that, at a constant macropore volume, the smaller the particle size, the higher the ethylene conversion and the lower the catalyst deactivation rate. The catalyst samples shown in FIGS. 1 and 2 were disposed in a packed, fixed-bed reactor.

FIG. 3 illustrates that, at a constant macropore volume, the smaller the particle size, the higher the ethylene conversion and the lower the catalyst deactivation rate. The catalyst samples in FIG. 3 were contained in a plurality of porous containers disposed in a fixed-bed, reactive-distillation reactor.

DETAILED DESCRIPTION OF THE INVENTION

Broadly, the present invention is directed to a process for the alkylation of aromatic hydrocarbons with an alkylating agent under liquid phase alkylation conditions in the presence of an alkylation catalyst comprising a silica-containing molecular sieve in a porous refractory inorganic oxide matrix.

Catalysts suitable for use in the present invention can be any silica-containing molecular sieve including, but not limited to, aluminosilicates, borosilicates, gallosilicates, and chromosilicates.

The preferred silica-containing molecular sieves are crystalline aluminosilicate zeolites which are based on an infinitely extending, three-dimensional network of $AlO_4$ and $SiO_4$ tetrahedra linked by the sharing of oxygen atoms. Chemically, the structural formula of a crystallographic unit cell of a zeolite may be expressed in terms of oxides, $$M_{x/n}[(AlO_2)_x(SiO_2)_y]mH_2O$$

where M is cation of valence n, m is the number of water molecules, and the sum of x and y is the total number of tetrahedra in the unit cell. The ratio of y/x can vary depending on the structure. The zeolite can be naturally-occurring or synthetic. Among the naturally-occurring zeolites which can be employed are faujasite, climoptolite, mordenite, and clachiasdite. Synthetic zeolites suitable for use in the present invention include X zeolite, Y zeolite, beta zeolite, L zeolite, and omega zeolite, preferably Y and beta zeolites.

A preferred Y zeolite is one that has been treated to make it more stable. Examples of suitable methods of stabilizing Y zeolites are disclosed in the U.S. Pat. Nos. 3,293,192; 3,449,070; 3,354,077; 3,493,519; 3,513,108; and 3,506,400. A preferred treatment method for stabilizing a Y zeolite is disclosed in U.S. Pat. No. 3,929,672. This method comprises ammonium-exchanging a Y zeolite to a sodium content between about 0.6–5.0 wt. %, calcining the ammonium-exchanged zeolite at a temperature of 600–1650 pressure of at least 0.2 psi to reduce the unit cell size to 24.40–24.64 Angstroms, and ammonium-exchanging the steam-calcined zeolite to replace at least 25 wt. % of the residium sodium ions and obtain a zeolite product of less than about 0.1–1.0 wt. % sodium. The same or a substantially similar zeolite is sold by Union Carbide Corporation as LZY-82.

In addition to a silica-containing molecular sieve, the catalyst of the present invention further comprises a porous refractory inorganic oxide matrix or binder which is combined, dispersed, or otherwise intimately admixed with the zeolite in order to have the physical strength and attrition resistance required in industrial use. Suitable inorganic binders include alumina, silica, clays, bauxite, zirconium oxide, hafnium oxide, titanium dioxide, zinc oxide, and magnesia. Suitable zeolite-binder composites contain about 1–99 wt. % of a zeolite component, preferably about 50–90 wt. % based on the weight of the zeolite-binder composite. The binder component makes up the remainder of the composite.

Suitable methods for compositing the zeolite materials with the binder can be found in U.S. Pat. Nos. 4,808,763 and 4,738,768 which are herein incorporated by reference.

An essential property of the catalyst of the present invention is that it possesses a pore volume of about 0.25–0.50 cc/g, preferably about 0.25–0.35 cc/g, most preferably about 0.30–0.35 cc/g in pores having a radius greater than about 450 Angstroms. Such pores are generally referred to as macropores which serve as "freeways" which improve diffusional access to the interior of the catalyst particles. As a practical matter, the upper limit on macropores is 10,000 Angstroms. If the volume of the macropores is too small, lower conversions and higher catalyst deactivation rates can occur because reactants and products cannot readily diffuse into and out of the catalyst. On the other hand, if the volume of the macropores is too large, the catalyst will have a low zeolite content per unit volume of catalyst, thereby resulting in lower conversion due to insufficient reactive sites available for alkylation catalysis. In order to achieve macropore volumes in the ranges required by the present invention binder must be present.

A catalyst possessing a macropore volume in the range of the present invention can be prepared by varying the zeolite and binder content of catalyst to achieve the desired result. Another suitable method of preparing such a catalyst is incorporating an organic material into the mix of a pelletized or extruded catalyst and burning out the organic material after the final catalyst particles are shaped and dried.

Another essential property of the alkylation catalyst of the present invention is a catalyst particle diameter of not more than about 1/32 of an inch, preferably not more than about 1/64 of an inch, most preferably not more than about 1/100 of an inch. As a practical matter, the minimum diameter of the catalyst particle can be about 1/1000 of an inch. Crushing catalyst particles below this minimum could significantly increase the cost of catalysts. Catalyst particle diameter is intended to be the diameter of the finished catalyst particle, i.e., the pelletized or extruded sieve-binder composite.

The catalyst can be disposed in any hydrocarbon conversion reactor including, but not limited to, a fixed-bed reactor, a fluidized-bed reactor, an ebullated-bed reactor, and a reactive-distillation reactor. In an ebullated bed, smaller catalyst particles may be required to allow proper dispersion of the catalyst. Since the catalyst of the present invention can have a particle size as low as about 1/100 of an inch, high pressure drops can be experienced in fixed-bed reactors. In a fixed-bed reactor, the catalyst can be packed into the reactor or contained in solid porous containers that are arranged to provide increased void volume within the reactor. In the case where the catalyt particles are packed into the reactor, a substantial pressure drop across the reactor can be experienced since the catalyst of the present invention can have a particle diameter of less than 1/32 of an inch. Accordingly, in a fixed-bed reactor, it is preferred to employ the catalyst particles in a plurality of solid porous containers, examples of which are disclosed in U.S. Pat. Nos. 4,215,011; 4,302,356; and 4,443,559. In a preferred embodiment, the catalyst particles are employed in a plurality of solid porous containers disposed in a fixed-bed, reactive-distillation reactor. The use of a reactive-distillation reactor has the added benefit of immedeately removed by fractionation monoalhylated aromatics from the reaction zone, thereby reducing the formation of undesirable polyalkylated aromatics.

Suitable aromatic hydrocarbons useful in this invention comprise benzene, toluene, ortho-xylene, metaxylene, para-xylene, ethylbenzene, ortho-ethyltoluene, meta-ethyltoluene, para-ethyltoluene, 1,2,3-trimethylbenzene, 1,2,4-trimethylbenzene, 1,3,5-trimethylbenzene or mesitylene, normal propylbenzene and isopropylbenzene. Higher molecular weight alkylaromatic hydrocarbons are also suitable and include aromatic hydrocarbons such as are produced by the alkylation of aromatic hydrocarbons with olefin polymers. Examples of such products are hexylbenzene, nonylbenzene, dodecyltoluene, and pentadecyltoluene. Other suitable alkylatable aromatic hydrocarbons include those having two or more aryl groups, such as diphenyl, diphenylmethane, triphenyl, and triphenylmethane. Examples of other alkylatable aromatic hydrocarbons within the scope of this invention include materials containing condensed benzene rings, such as naphthalene, alpha-methylnaphthalene, beta-methylnaphthalene, anthracene, phenanthrene, and naphthacene. Of the above aromatic hydrocarbons for use in the present invention, benzene, toluene and xylene are preferred.

A suitable source of aromatic hydrocarbons is a refinery total reformate stream. In general, such a stream has about 25 to 35 wt. % paraffins, 0.5–2 wt. % naphthenes, and 60–80 wt. % aromatics. A typical refinery total reformate stream has a composition in mole percent of about percent: 0.5% $C_4$ paraffins, 8.9% $C_5$ paraffins, 13.2% $C_6$ paraffins, 5.5% $C_7$ paraffins, 0.8% $C_8$ paraffins, 0.1% $C_9$ paraffins, 0.3% $C_5$ naphthenes, 0.3 $C_6$ naphthenes, 0.2% $C_7$ naphthenes, 0.1% $C_8$ naphthenes, 8.4% $C_6$ aromatics, 20.3% $C_7$ aromatics, 19.8% $C_8$ aromatics, 13.2% $C_9$ aromatics, 6.5% $C_{10}$ aromatics, and 1.9% $C_{11}+$ aromatics. Preferably, the aromatic source is a light fraction of the total reformate stream. In general, such a stream has about 40–60 wt. % paraffins, 1–3 wt. % naphthenes, and 40–50 wt. % aromatics. A typical light refinery reformate stream has a composition in mole percent of about 1.6% $C_4$ paraffins, 12.2% $C_5$ paraffins, 20.6% $C_6$ paraffins, 12.8% $C_7$ paraffins, 5.5% $C_8$ paraffins, 0.5% $C_9$ paraffins, 0.6% $C_5$ naphthenes, 0.7% $C_6$ naphthenes, 0.4% $C_8$ naphthenes, nil $C_9$ naphthenes, 10.9% C₆ aromatics, 28.7% C₇ aromatics, and 4.6% C₈ aromatics.

Alkylating agents suitable for use in the present invention are olefins, alcohols, alkenes, alkynes, aldehydes, ethers, acetylenes, and any other acyclic compounds having at least one reactive alkyl radical. Suitable alcohols are methanol, ethanol, n-propanol, and isopropanol. The olefins can be $C_2$ to $C_{20}$ olefins, preferably $C_2$–$C_{12}$ olefins, including normal and branched forms thereof. For example, suitable olefins are ethylene, propylene, butylene, isobutylene, 1-pentene, 1-hexene, 2-hexene, cyclohexene, methyl cyclohexene, 2,3-dimethyl-1-pentene, 1-octene, diisobutylene, 1-nonene and 1-decene, dodecene and the like. In a preferred embodiment the olefin is a $C_2$–$C_4$ olefin. The preferred alkylating agents are ethylene and propylene.

The present invention can be practiced with alkylating agents wherein the ethylene and propylene olefinic hydrocarbons are present in gas streams. The gas streams are present in petroleum refineries from various refinery installations including thermal cracking units, catalytic cracking units, thermal reforming units, coking units, and polymerization units. A typical analysis in mole percent for a suitable refinery off-gas is as follows: 4.0% nitrogen, 0.2% carbon monoxide, 5.4% hydrogen, 37.8% methane, 10.3% ethylene, 24.7% ethane, 6.5% propylene, 10.7% propane, and 0.5% C₄ hydrocarbons.

A suitable aromatic to alkylating agent ratio in the reaction zone can be about 1:1 to 100:1, preferably 4:1 to 25:1.

An essential process condition of the present invention is that the alkylation reaction occur in a liquid phase. The presence of a liquid phase in the reaction zone decreases catalyst deactivation rates. In a preferred embodiment, the alkylation reaction occurs in a liquid continuous phase which is defined as a liquid phase having a continuous phase of vapor bubbling up therethrough. The source of the vapor can be external to the alkylation reactor, for example, a gaseous alkylating agent, or internal to the alkylation reactor, for example, vapor generated from a reboiler of a fixed-bed, reactive-distillation reactor. Other process conditions suitable for use in the present invention include a temperature of about 250–750 deg F., preferably about 300–450 deg F., a pressure of about 1–100 atms, preferably about 10–30 atms, and a weight hourly space velocity of about 0.1–20 hr⁻¹.

EXAMPLE 1

In this example, three (3) catalysts were prepared and tested to determine the effect of macropore volume on ethylene conversion, catalyst activity, and catalyst deactivation rate. In this example the particle sizes of two of the catalysts were held constant while the macropore volume was varied.

Table 1 includes a description of the properties of the catalysts and performance data related to catalyst activity and deactivation rate. Table 1 is divided into two sections, catalyst properties and catalyst performance. The information given under catalyst properties section was obtained from three standard analytical tests--x-ray diffraction, temperature programmed desorption, and mercury porosimetry. Temperature programmed desorption is an analytical method that is routinely used to measure micropores and mesopores of catalyst (micropores having a radius of less than about 20 Angstroms and mesopores having a radius of about 20–450 Angstroms). Mercury porosimetry is an analytical method routinely used to measure mesopores and macropores (macropores being greater than about 450 Angstroms).

TABLE 1

|  | A | B | C |
|---|---|---|---|
| Catalyst Properties |  |  |  |
| Diameter, inches | 1/16 | 1/32 | 1/32 |
| X-ray Diffraction: |  |  |  |
| Unit Cell Size, Angs. | 24.5067 | 24.5192 | 24.4427 |
| Volume Angs.³ | 14718 | 14741 | 14603 |
| % Crystallinity | 65 | 60 | 61 |
| Al/unit cell | 36.4 | 37.8 | 29.0 |
| Temp. Programmed Desorption: |  |  |  |
| Surface Area, m²/g | 549 | 549 | 519 |
| Pore Volume, cc/g | 0.24 | 0.22 | 0.29 |
| Micropore Volume, cc/g | 0.196 | 0.189 | 0.176 |
| % Zeolite | 77 | 74 | 69 |
| Mercury Porosimetry: |  |  |  |
| Total Volume, cc/g | 0.369 | 0.468 | 0.42 |
| Avg. Pore Radius, Angs. | 79 | 100 | 66 |
| Macropore Volume, cc/g | 0.17 | 0.31 | 0.20 |
| % Na | — | 0.116 | 0.113 |
| Catalyst Performance |  |  |  |
| Activity after 24 hrs. | 1.0 | 2.4 | 1.7 |
| Activity after 50 hrs. | 0.68 | 2.2 | 1.4 |
| % Deactivation Activity loss 24–50 hrs. | 32 | 8 | 18 |
| Deactivation Rate % activity loss/hr. | 1.23 | 0.30 | 0.69 |

Catalyst A was commercially available ultrastable Y zeolite, 1/16 inch diameter extrudates LZY-82 manufactured by Union Carbide.

Catalyst B was prepared by dry-mixing 80 wt. % LZY-82 powder with 20 wt. % PHF alumina powder binder. 400 g of distilled water was then added. This material was then blended using an intensive mixer. The material was then extruded into 1/32 inch diameter extrudates and more distilled water was added during the extruding process. The extruded catalyst was dried at 250 deg F. overnight and then calcined at 900 deg F. for 3 hr.

Catalyst C was prepared by mixing 80 wt. % LZY-82 powder with 20 wt. % PHF alumina and adding water. The excess water was then removed in a filter press. This mixture was then extruded into a 1/32 inch diameter extrudates. The extruded catalyst was then calcined for 3 hr at 1000 deg F.

The catalysts were then packed into a fixed-bed, tubular, stainless steel reactor. The toluene and ethylene entered the reactor at the bottom and exited the reactor at the top. The bottom section of the reactor contained inert 1/64 inch alumina chips or ⅛ inch ceramic balls. The middle section of the reactor consisted of 10 g of catalyst particles diluted with fractionation tower packing. The top section of the reactor was filled with ⅛ inch ceramic balls or glass wool to hold the catalyst bed in place.

The reactor conditions for the test were 370 deg F. at 300 psig. The feed consisted of 104 g/hr of toluene, 9.1 g/hr of ethylene, and 6.4 g/hr of methane.

The key comparison in Example 1 is between Catalysts B and C. In Table 1, under the catalyst properties section, it is shown that Catalyst B had a diameter of 1/32 of an inch and a macropore volume of 0.31 cc/g. Also in this section of Table 1, it is shown that Catalyst C had the same diameter, 1/32 of an inch, and a lower macropore volume, 0.20 cc/g. In Table 1, under the catalyst performance section, it is shown that Catalyst B had an activity of 2.2 after 50 hours of operation, and Catalyst C had an activity of 1.4 after 50 hours of operation. Further in Table 1, under the catalyst performance section, it is shown that Catalyst B had a deactivation rate of 0.3, and Catalyst C had a deactivation rate of 0.69. Accordingly, Table 1 shows that, at a constant particle diameter, the higher the macropore volume the higher the activity and the lower the deactivation rate.

Figure 1:
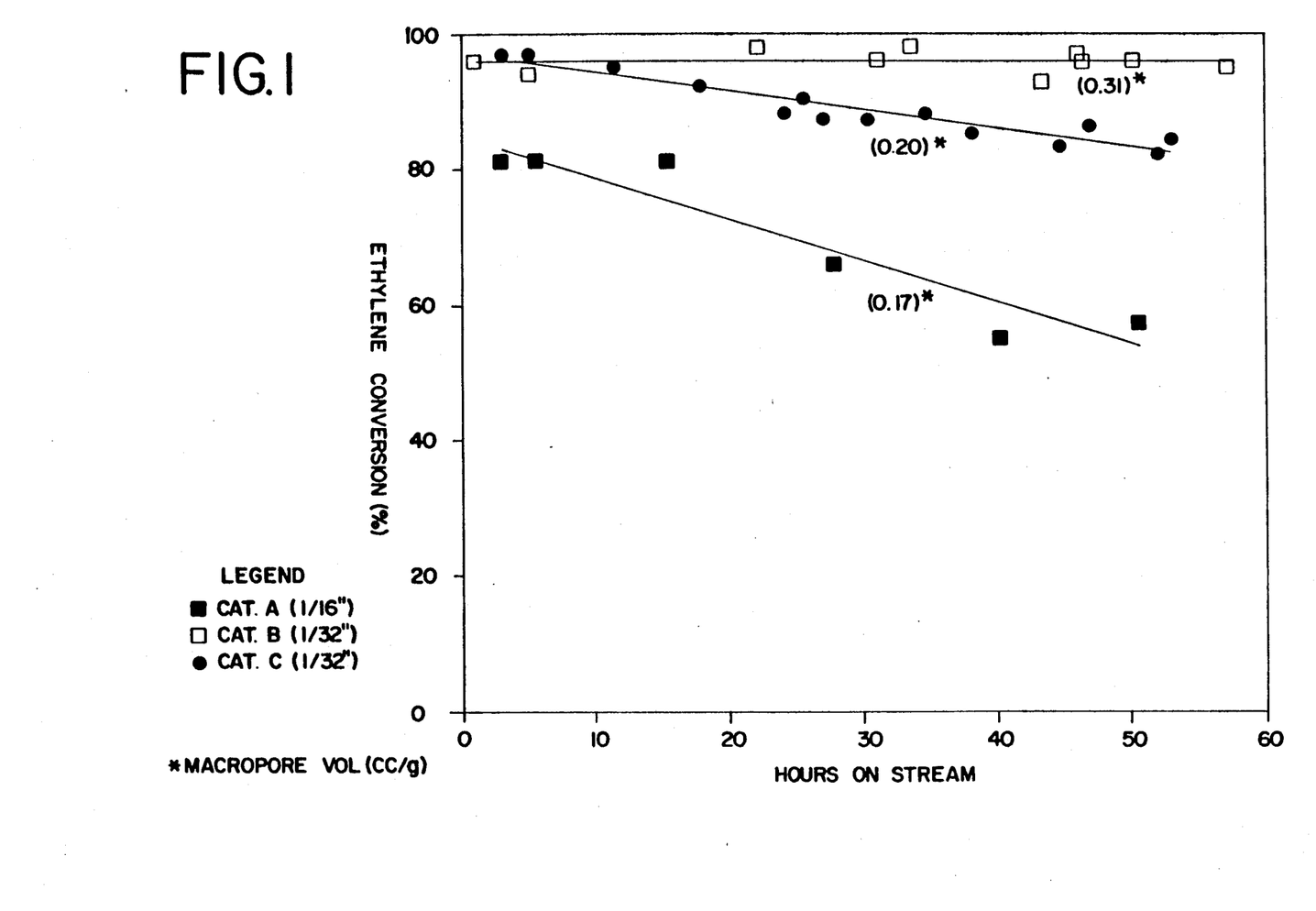
FIG. 1 is a graph of the ethylene conversion versus hours on stream for catalysts having a constant particle diameter and different macropore volumes.

Plots comparing ethylene conversion versus time for Catalysts B and C are shown in FIG. 1. Catalyst B (open squares), which had a particle size of 1/32 of an inch and a macropore volume of 0.31 cc/g, had an initial ethylene conversion of about 95% and maintained that conversion for about 50 hr of operation. Catalyst C (dark circles), which had a particle size of 1/32 of an inch and a macropore volume of 0.20 cc/g, had an initial ethylene conversion comparable with Catalyst B, but fell to about 85% after 50 hr on line. Figure illustrates that, at a constant particle diameter, the higher the macropore volume, the higher the ethylene conversion and the lower the catalyst deactivation rate.

FIG. 1 also contains data for Catalyst A which is designated by the dark squares. Catalyst A, which had a macropore volume of 0.17 cc/g and a particle size of 1/16 of an inch, had an initial ethylene conversion of about 80% and dropped at a sharp rate to a conversion of about 55% after 50 hours on line. Catalyst A, the commercially-available LZY-82 catalyst showed the poorest performance of all the catalysts tested. Accordingly, it fell outside the inventive range for macropore volume and catalyst particle size.

EXAMPLE 2

Figure 2:
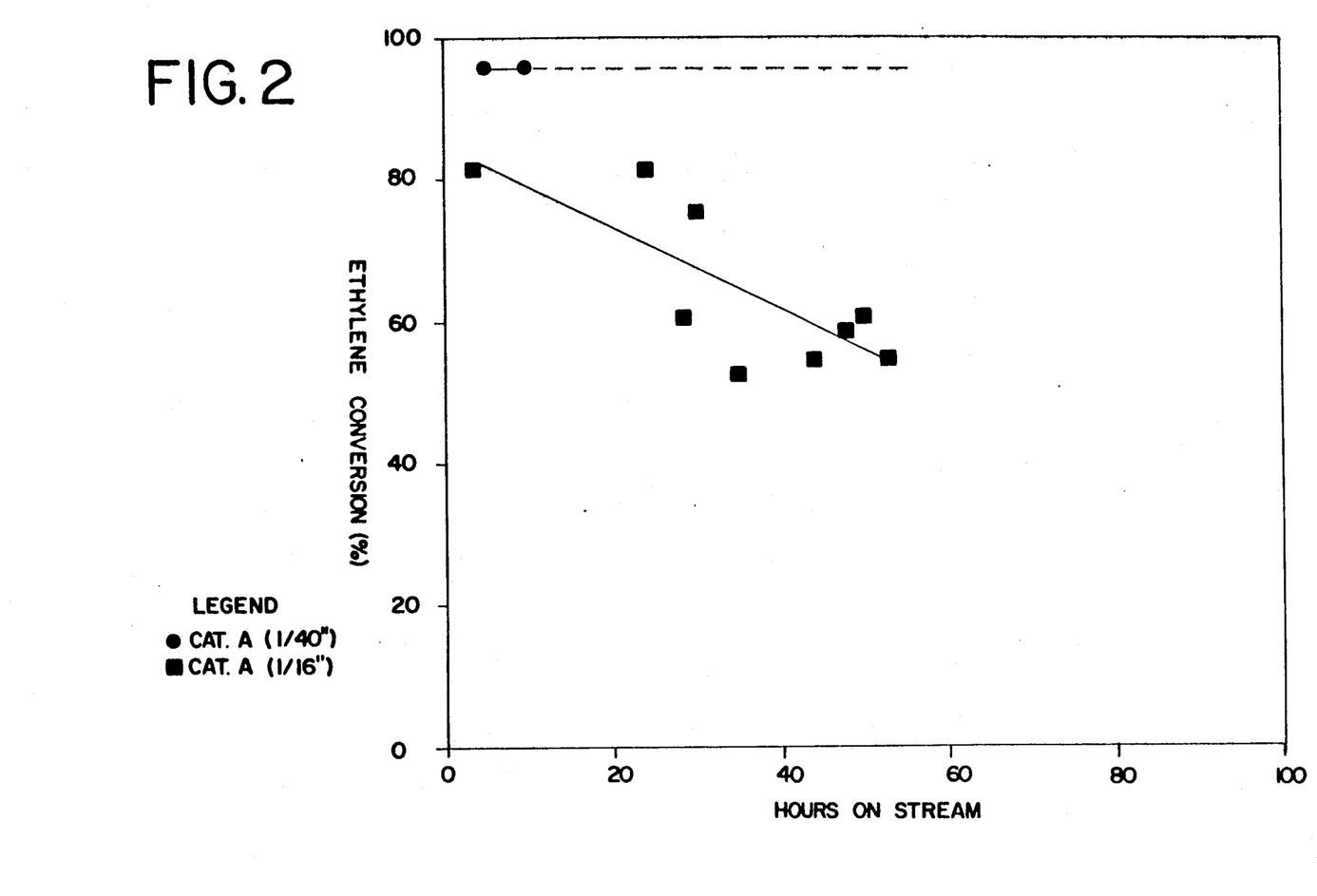
FIG. 2 is a graph of ethylene conversion versus hours on stream for catalyst samples having a constant macropore volume and different particle diameters.

The purpose of this example was to show the effects of catalyst particle diameter on ethylene conversion. FIG. 2 plots ethylene conversion versus hours on stream for two different particle diameters of Catalyst A of Example 1. The dark squares represent the original 1/16 inch diameter Catalyst A particles. The dark circles represent Catalyst A particles that were ground to 20–40 mesh diameter particles. For comparison purposes the 20–40 mesh (0.0331–0.0165 inches) dimension was converted to an average diameter of 0.0250 or 1/40 inches.

Both Catalyst A samples had a macropore volume of 0.17 cc/g. The reactor and test conditions used were the same as those described in Example 1.

As shown in FIG. 2, the 1/40 inch average diameter Catalyst A particles had an initial conversion of about 95% and maintained that level for 10 hr. Extrapolation of the data, as shown by the dotted line would estimate an ethylene conversion of 95% after 50 hr on stream. The 1/16 inch diameter Catalyst A particles had an initial conversion of about 80% and fell to a conversion of about 55% after 50 hr on stream. Accordingly, FIG. 2 illustrates that, at a constant macropore volume, the smaller the particle diameter, the higher the ethylene conversion and the lower the catalyst deactivation rate.

A comparison of the 1/40 inch Catalyst A particles shown in FIG. 2 and the 1/32 inch Catalyst B particles of FIG. 1 indicates comparable performance. This could be attributed to particle size effects. As previously stated, the description of the Catalyst A particle diameter as being 1/40 inches was actually an average representing a particle diameter distribution of about 0.0331–0.0165 inch. Therefore, a substantial portion of the Catalyst A particles described as having 1/40 inch diameters had actual diameters that were significantly smaller.

EXAMPLE 3

The purpose of this Example is to determine whether the positive effects of small diameter catalyst particles on ethylene conversion and catalyst deactivation rate hold true when the catalyst particles are disposed in a fixed-bed, reactive-distillation reactor.

The reactor used in this experiment was a fixed-bed, reactive-distillation unit having an outside diameter of 1 inch and a length of 21 feet. The top and bottom sections of the reactor were packed with fractionation packing. The middle section of the reactor was packed with Catalyst A particles of Example 1 having the desired particle diameter. The catalyst had been placed in cloth catalyst bags and wrapped in demister packing prior to placing it in the reactor. The top section was 4 feet, the middle 6 feet, and the bottom section was 11 feet in length.

The feed to the reactor consisted of both a gaseous olefinic stream and a liquid aromatic stream. The gaseous olefinic stream was 37 wt. % ethylene and 63 wt. % methane. The liquid aromatic stream consisted of a reformer product stream containing 45 wt. % toluene and 8 wt. % benzene. The process conditions for the reactor were a temperature of 340 degrees F., a pressure of 80 psig, an aromatic feed rate of 335 g/hr and an ethylene feed rate of 28 g/hr.

The test consisted of two runs. The first run used 235 g of 1/16 inch diameter Catalyst A particles. The second run used 272 g of 1/40 inch average diameter Catalyst A particles. In these runs, the gaseous olefinic stream was fed at the bottom and the product removed from the top and bottom via fractionation. The aromatic liquid feed entered in the middle of the unit above the catalyst zone. The aromatic liquid feed was held in the catalytic distillation unit so that the catalyst zone was liquid-filled and had gas bubbling up therethrough.

Figure 3:
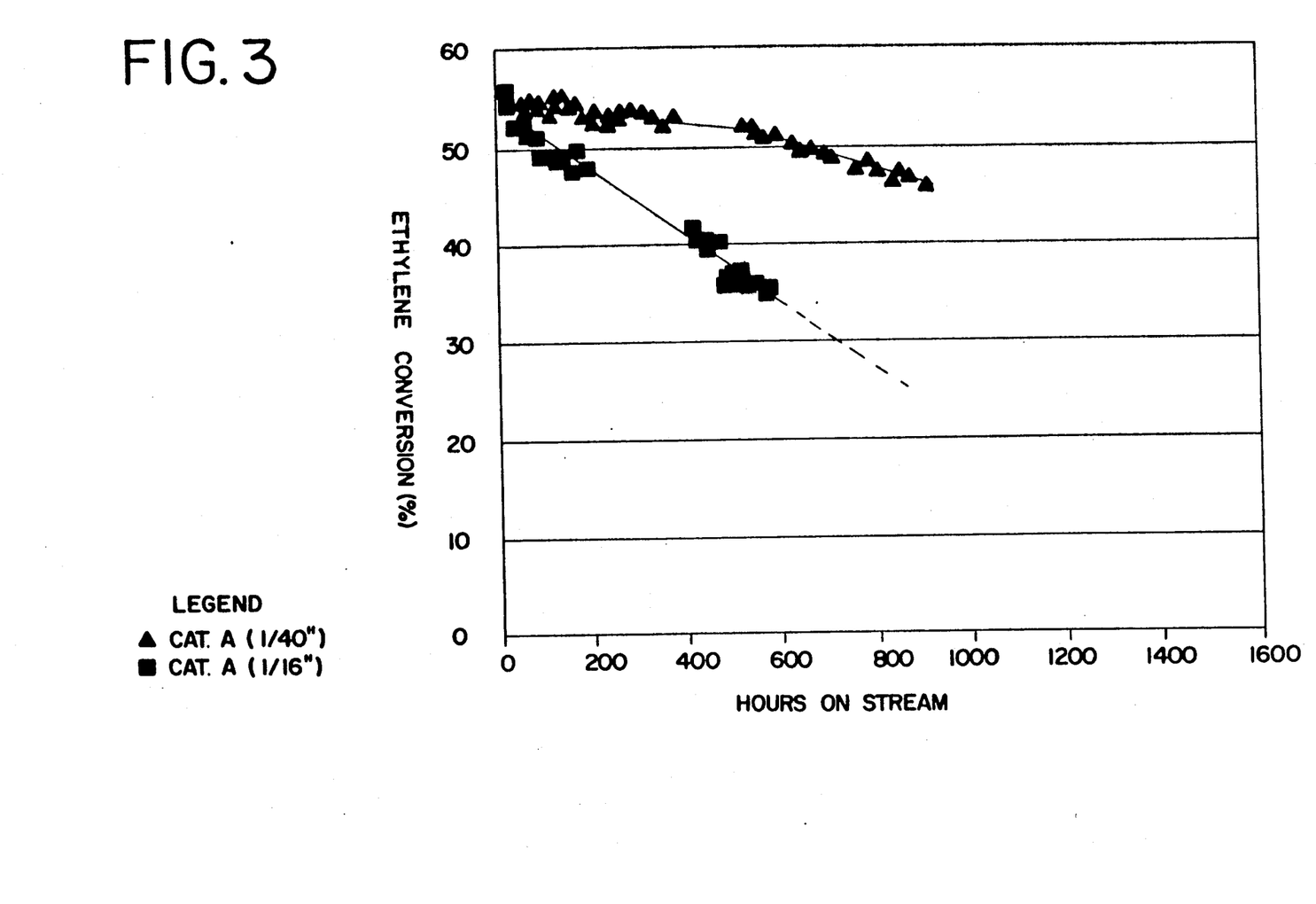
FIG. 3 is a graph of ethylene conversion versus hours on stream for catalyst samples having a constant macropore volume and different particle diameters.

The results of these runs are shown in FIG. 3. The smaller 1/40 inch diameter Catalyst A particles had an initial ethylene conversion of about 55% and fell to an ethylene conversion of about 46% after about 900 hours on stream. The larger 1/16 inch Catalyst A particles had an initial ethylene conversion of about 57% and fell to an ethylene conversion of about 35% after about 600 hours on stream. An extrapolation of the data, as shown by the dotted line, would estimate an ethylene conversion of about 26% after 900 hours on stream.

FIG. 3 illustrates that the trend found in FIG. 2, i.e., the smaller the catalyst particle size, the higher the ethylene conversion and the lower the catalyst deactivation rate, also holds true for fixed-bed, reactive-distillation reactors.

EXAMPLE 4

In Example 4, the macropore volume was held constant while the particle diameter was varied to determine the effect of particle size on ethylene conversion.

The catalyst used in this example was ⅛ inch Catalyst A particles of Example 1. The catalyst had a macropore volume of 0.17 cc/g, a zeolite content of 80 wt. %, and an alumina content of 20 wt. %.

The reactor used in the experiment was made of an 18 inches in length of ⅜ inch diameter stainless steel tubing. Both the top and bottom of the reactor were fitted with ⅜ inch diameter Swagelok tees. An ⅛ inch diameter thermowell was centered in the reactor and extended from the top to the bottom of the reactor where it was inserted into the ¼ inch diameter gas inlet tube. Positioning the thermowell in this manner aided in keeping it centered throughout the reactor and in dispersing the gas mixture. Both liquid and gas inlets were at the bottom of the reactor.

The bottom of the reactor was packed with glass wool. On top of that was 6.0 inches of an inert packing of alpha alumina. In the experiments, two different sizes of alpha alumina were used; they were 12-20 mesh (about 1/20 inch) average diameter and 40-60 mesh (about 1/77 inch) average diameter. Next was the catalyst bed which contained roughly 0.9 g of catalyst and 2.8 g of gamma alumina. The catalyst zone was 3.0 inches long and contained 6.0 ml of catalyst and gamma alumina. For these tests, three different sizes were used in the catalyst bed. They were 12-20 mesh (about 1/20 inch) average diameter, 20-40 mesh (about 1/40 inch) average diameter, and 40-60 mesh (about 1/77 inch) average diameter. In all cases, the inert gamma alumina diluent was of the same mesh size as the catalyst.

The essential parts of the experimental unit were the toluene feed system, which was a 350 ml ISCO high pressure pump, and a gas inlet system for either nitrogen or the feed gas, which was a 20 mol % ethylene and 80 mol % methane mixture. The unit was run in an upflow manner, and the pressure was chosen so that the catalyst bed was essentially flooded with toluene. Downstream of the reactor were liquid knockouts and a gas flow controller. The furnace was a three zone furnace with each zone controlled by a temperature controller. In addition, there was a traveling thermocouple in the center of the reactor to measure the reaction temperature.

To start the unit, nitrogen purged the system for at least 30 min. The ISCO pump for toluene was turned on, and the flow of the hydrocarbon gases were started. About 30 min after the flows had started, power to the three heaters was turned on. Flow rates for the gas and liquid were established at 100 ml (of gas)/min and 40 ml (of toluene)/hr. For the unit, the product gas flow was controlled. The inlet gas flow was calculated from the outlet gas flow and the composition of the gas before and after reaction. Gas and liquid samples were taken at 30 min intervals. The liquid samples were weighed, and both the liquid and gas samples were analyzed on Varian GC using a 60 meter capillary column. The column was prepared by J&W Scientific, had an internal diameter of 0.32 mm and was coated with a 1.0 micron DB-1 film.

For these experiments, different diameter sizes of catalysts and inert diluent before and after the catalyst bed were used. The experiments were all carried out at 300 psig.

The results of the variation of catalyst diameter on conversion are given in Table 2. Each data point represents an average of three to six data experimental results.

TABLE 2

The Effect of Catalyst Diameter on the Conversion of Ethylene

| | Catalyst Diameter (approx. avg. inches) | | |
|---|---|---|---|
| | 1/20 | 1/40 | 1/77 |
| @ 320 deg F. | 50.8% | 55.7% | 64.4% |
| @ 360 deg F. | 58.4% | 71.5% | 90.2% |
| @ 400 deg F. | 64.8% | 82.9% | 96.1% |

In comparing the different diameter sizes shown in Table 2, it is important to recognize that the macropore volume does not vary. In Table 2, at 320 deg F., the 1/20 inch average diameter catalyst particles had an ethylene conversion of 50.8%. As the diameter of the catalyst particles decreased to 1/40 and 1/77 inches, the ethylene conversion increased to 55.7% and 64.4%, respectively. Table 3 also shows that the higher the temperature, the greater the effect of particle size on the ethylene conversion. At 400 deg F., the 1/20 inch catalyst had an ethylene conversion of 64.8%. As the diameter of the catalyst particle decreased to 1/40 and 1/77 inches, the ethylene conversion increased to 82.9% and 96.1%, respectively. Accordingly, Table 2 shows that, at a constant macropore volume, the smaller the catalyst diameter the higher the ethylene conversion. Table 2 also shows that higher temperatures accentuate this effect.

We claim:

1. An aromatic alkylation process comprising the steps of contacting a feedstock comprising aromatic hydrocarbons with an alkylating agent under liquid phase alkylation conditions in the presence of a catalyst comprising a silica-containing molecular sieve in a porous refractory inorganic matrix wherein said catalyst possesses a pore volume of about 0.25-0.50 cc/g in pores having a radius greater than about 450 Angstroms and a catalyst particle diameter of not more than about 1/40 of inch, said catalyst being employed in a plurality of solid, porous containers disposed in a fixed-bed, reactive-distillation reactor.

2. A method of claim 1 wherein said alkylating agent comprises an olefinic hydrocarbon.

3. A method of claim 2 wherein said olefinic hydrocarbon comprises an olefinic hydrocarbon selected from the group consisting of ethylene and propylene.

4. A method of claim 1 wherein said aromatic hydrocarbon is selected from the group consisting of benzene, toluene, and xylene.

5. A method of claim 1 wherein said molecular sieve comprises a crystalline aluminosilicate zeolite.

6. A method of claim 5 wherein the zeolite is selected from the group consisting of a Y zeolite and a beta zeolite.

7. A method of claim 1 wherein the pore volume is about 0.25-0.35 cc/g.

8. A method of claim 7 wherein the pore volume is about 0.30-0.35 cc/g.

9. A method of claim 1 wherein the catalyst particle diameter is not more than about 1/64 of an inch.

10. A method of claim 9 wherein the catalyst particle diameter is not more than about 1/100 of an inch.

11. An aromatic alkylation process comprising the steps of contacting a liquid aromatic hydrocarbon selected from the group consisting of benzene, toluene, and xylene with an alkylating agent comprising an olefinic hydrocarbon under liquid continuous phase alkylation conditions in the presence of a catalyst comprising a crystalline aluminosilicate zeolite in a matrix selected from the group consisting of silica and alumina wherein said catalyst possesses a pore volume of about 0.25–0.35 cc/g in pores having a radius greater than 450 Angstroms and a catalyst particle diameter of not more than about 1/64 of an inch, said catalyst being employed in a plurality of solid, porous containers disposed in a fixed-bed reactive-distillation reactor.

12. A method of claim 11 wherein said olefinic hydrocarbon is selected from the group consisting of ethylene and propylene.

13. A method of claim 11 wherein said zeolite comprises an beta zeolite.

14. A method of claim 11 wherein the macropore volume is about 0.30–0.35 cc/g.

15. A method of claim 11 wherein the catalyst particle diameter is not more than about 1/100 of an inch.

16. An aromatic alkylation process comprising the steps of contacting a liquid aromatic hydrocarbon selected from the group consisting of benzene, toluene, and xylene with an alkylating agent selected from the group consisting of ethylene and propylene under liquid continuous phase alkylation conditions in the presence of catalyst consisting essentially of beta zeolite in a matrix consisting essentially of alumina wherein said catalyst possesses a pore volume of about 0.30–0.35 cc/g in pores having a radius greater than about 450 Angstroms and a catalyst particle diameter of not more than about 1/100 of an inch, said catalyst being employed in a plurality of solid porous containers disposed in a fixed-bed, reactive-distillation reactor.

* * * * *